United States Patent
Elliott et al.

(10) Patent No.: US 7,157,593 B2
(45) Date of Patent: *Jan. 2, 2007

(54) FERROUS PICRATE PRODUCED BY A PROCESS UTILIZING A NON-POWDERED METALLIC IRON

(75) Inventors: Alan F. Elliott, South Melbourne (AU); David M. Stewart, Taylorsville, UT (US)

(73) Assignee: RDI Construction, South Point, OH (US)

( * ) Notice: Subject to any disclaimer, the term of this patent is extended or adjusted under 35 U.S.C. 154(b) by 472 days.

This patent is subject to a terminal disclaimer.

(21) Appl. No.: 10/746,242

(22) Filed: Dec. 23, 2003

(65) Prior Publication Data

US 2004/0158089 A1 Aug. 12, 2004

Related U.S. Application Data

(63) Continuation-in-part of application No. 10/150,602, filed on May 16, 2002, now Pat. No. 6,969,773.

(51) Int. Cl.
 *C07F 15/00* (2006.01)
 *C10L 1/22* (2006.01)

(52) U.S. Cl. ............................ 556/150; 44/323; 44/367

(58) Field of Classification Search ................. 556/150; 44/323, 367
See application file for complete search history.

(56) References Cited

U.S. PATENT DOCUMENTS

| 2,506,539 | A | 5/1950 | Boardman |
| 3,282,858 | A | 11/1966 | Simmons |
| 4,073,626 | A | 2/1978 | Simmons |
| 4,099,930 | A | 7/1978 | Webb |
| 4,129,421 | A | 12/1978 | Webb |
| 4,265,639 | A | 5/1981 | Scholtz |
| 4,397,654 | A | 8/1983 | T Hart |
| 4,424,063 | A | 1/1984 | Hart |
| 5,087,268 | A | 2/1992 | Parish |
| 5,359,103 | A | 10/1994 | Elliott |
| 5,562,742 | A | 10/1996 | Kolp et al. |
| 5,720,783 | A | 2/1998 | Elliott |
| 5,925,153 | A | 7/1999 | Riegel |
| 6,670,495 | B1 | 12/2003 | Stewart |
| 6,833,466 | B1 * | 12/2004 | Elliott et al. ................ 556/150 |
| 2003/0213166 | A1 | 11/2003 | Stewart |
| 2003/0213167 | A1 | 11/2003 | Stewart |
| 2004/0158089 | A1 | 8/2004 | Elliott et al. |

FOREIGN PATENT DOCUMENTS

| AU | B-63110/90 | 6/1991 |
| AU | B-57904/90 | 9/1991 |
| DE | 27 59 055 A1 | 12/1979 |
| WO | WO 94/26689 | 11/1994 |

* cited by examiner

*Primary Examiner*—Porfirio Nazario-Gonzalez
(74) *Attorney, Agent, or Firm*—TraskBritt

(57) ABSTRACT

A fuel additive containing ferrous picrate produced by a process involving placing a non-powdered metallic iron, such as wire composed of an alloy of iron or steel wool, in any solution of picric acid in a solvent that is known in the art for reacting with iron to produce ferrous picrate. The wire can be suspended in the solution or placed upon the bottom of a reaction vessel that holds the solution. Preferably the wire is loosely coiled, at least when placed upon the bottom of a reaction vessel. Also preferably, after a concentrated fuel additive has been prepared, to the concentrate is added so much of a pre-mix solution produced by the steps of (a) dissolving picric acid in the same kind of solvent that was utilized to produce the solution into which the steel wool was placed and (b) removing water from the precursor to the pre-mix solution thus produced and so much of the same kind of alcohol that was utilized to produce the solution into which the steel wool was placed that the final product produced thereby contains approximately 1.9 percent free picric acid and 15 to 16 percent of the alcohol.

8 Claims, No Drawings

US 7,157,593 B2

FERROUS PICRATE PRODUCED BY A PROCESS UTILIZING A NON-POWDERED METALLIC IRON

CROSS-REFERENCE TO RELATED APPLICATIONS

This application is a continuation-in-part of U.S. Ser. No. 10/150,602, filed May 16, 2002, now U.S. Pat. No. 6,969,773, the contents of which are incorporated in its entirety by this reference.

TECHNICAL FIELD

This invention relates to a fuel additive produced by a process for producing ferrous picrate utilizing wire.

BACKGROUND

There are many patents dealing with process for producing ferrous picrate fuel additives.

These include U.S. Pat. Nos. 2,506,539; 3,282,858; 4,073,626; 4,099,930; 4,129,421; 4,265,639; 4,424,063; 5,087,268; 5,359,103; 5,720,783; and 5,925,153.

Only U.S. Pat. Nos. 5,087,268 and 5,925,153 employ metallic iron; and these both utilize powdered elemental iron. The large surface area of powdered elemental iron facilitates the desired reaction.

SUMMARY OF THE INVENTION

Surprisingly, it has been discovered that a non-powdered metallic iron, such as wire comprised of an iron alloy or steel wool can produce favorable reaction rates.

Preferably the wire is loosely coiled, and either the wire or the steel wool is suspended in the reaction vessel or placed upon the bottom of the reaction vessel.

The product produced by this process does not contain the particles of iron found in fuel additives produced from iron in accordance with the processes of the prior art.

DESCRIPTION OF THE PREFERRED EMBODIMENT

The present process can employ any solution of picric acid in a solvent that is known in the art for reacting with iron to produce ferrous picrate.

Preferably, however, a solution that is approximately three percent picric acid (i.e., three grams of picric acid per one hundred milliliters of solvent) is produced by dissolving picric acid in a solvent. Since dry picric acid is explosive, the picric acid is supplied with water. Acceptable solvents are an aromatic solvent such as benzene, toluene, or xylene or a high aromatic petroleum fraction such as Solvent 100, although all other aromatic solvents and high aromatic petroleum fractions disclosed in the art to be used for a similar purpose are also acceptable and will hereinafter simply be termed aromatic solvents and high aromatic petroleum fractions used in the art. A practical percentage which can be achieved within a reasonable time is 2.8 percent. The more picric acid which is dissolved, the better. It is, however, extremely difficult to dissolve significantly more than three percent. The percentage of picric acid which has been dissolved is determined analytically, preferably by titration.

After having combined the picric acid with the solvent, water is removed from the solution using any technique that is well known in the art. Preferably, though, settling is allowed to occur so that the water is vertically separate from the solution of picric acid in solvent. Then the top layer can be removed by decantation or siphoning, or the bottom layer can be removed by draining. One of the various alternate methods for removal is centrifugal separation; another is azeotropic distillation.

The solution resulting from this preferred mixture is termed a pre-mix (as also, for the purposes of this patent application, is any solution of picric acid in a solvent, after such solution has been dewatered, that is prepared in accordance with the art of preparing ferrous picrate; such solution before dewatering is termed a precursor to the pre-mix solution) and has subsequently added to it an aliphatic alcohol. A non-exclusive list of acceptable aliphatic alcohols includes ethanol, isopropanol, and butanol. Butanol is preferred. It is preferable to add the aliphatic alcohol to the pre-mix rather than adding the pre-mix to the aliphatic alcohol in order to prevent the precipitation of some of the dissolved picric acid. Preferably, 25 percent butanol is combined with 75 percent pre-mix on a volume basis.

To the resultant solution some water, preferably 0.1 to 0.5 percent and most preferably approximately 0.1 percent, is added. This is to control the quantity of water since some is necessary for the desired reaction to occur, but an excess amount causes instability and degradation in the product.

Preferably, the solution is agitated after the initial combination of ingredients and each addition of an ingredient.

A non-powdered metallic iron such as, for example, wire composed of an alloy of iron or steel wool is suspended in the solution, either any solution known in the art for producing ferrous picrate from iron or the preferred solution discussed above, or is placed upon the bottom of a reaction vessel that contains the solution. Preferably the wire is loosely coiled, at least when placed upon the bottom of a reaction vessel. Suspension of the wire or the steel wool can be accomplished using any material that will not react with the substances in the solution; stainless steel is, however, preferred for this purpose.

The non-powdered metallic iron, such as wire or steel wool, preferably, but not necessarily, contains 0.2 to 5.0 percent, by weight, of carbon, manganese, phosphorus, sulfur, and silicon alloyed with the iron.

The solution is preferably agitated after the non-powdered metallic iron, such as wire or steel wool, has been introduced. The product resulting from reaction of the picric acid with the non-powdered metallic iron to produce ferrous picrate is termed a "concentrate." A preferred concentration of iron in the concentrate is 1425 ppm.

It has experimentally been determined, however, that degradation of the product over time is minimized, i.e., stability is maximized, when the solution contains approximately 1.9 percent free (dissolved but unreacted) picric acid and 15 to 16 percent aliphatic alcohol, preferably butanol. A selected concentration of iron less than that of the concentrate is then achieved by combining the requisite amounts of concentrate, pre-mix, and aliphatic alcohol to attain the desired concentration of iron while also containing approximately 1.9 percent free picric acid and 15 to 16 percent of the alcohol. For stability, if the water content if higher than 0.25 percent, the water content may be reduced to about 0.25 percent or less by adding dry solvent. This is termed the final product.

Either the concentrate or the final product is appropriately termed a fuel additive.

In another embodiment, after a concentrated fuel additive has been prepared, to the concentrate is added so much of a pre-mix solution produced by the steps of (a) dissolving picric acid in the same kind of solvent that was utilized to produce the solution into which the non-powdered metallic iron, such as steel wool, was placed and (b) removing water from the precursor to the pre-mix solution thus produced and so much of the same kind of alcohol that was utilized to produce the solution into which the steel wool was placed that the final product produced thereby contains approximately 1.9 percent free picric acid and 15 to 16 percent of the alcohol.

A further decrease in degradation is caused by the fact that the use of non-powdered metallic iron, i.e., wire or steel wool, instead of small particles of iron, such as filings or powder, precludes small particles of iron from being in the concentrate and the final product.

The following example illustrates this process.

EXAMPLE 1

A mixture of 22.5 parts of picric acid and 750 parts of Solvent 100 was agitated in a container until the picric acid was dissolved. Then 250 parts of butanol were added to the solution. This was then thoroughly mixed. Next, 1 part of tap water was added to the solution; and the contents were again thoroughly mixed. Then 8 parts of a non-powdered metallic iron such as, for example, steel wire were suspended in the solution. The contents of the container were then agitated for 1 hour and 35 minutes to produce a ferrous picrate solution containing 1,425 parts per million of ferrous iron. In another embodiment, the non-powdered metallic iron may comprise steel wool.

As used herein the term "preferable" or "preferably" means that a specified element or technique is more acceptable than another but not that such specified element or technique is a necessity.

What is claimed is:

1. A process for producing a fuel additive containing ferrous picrate, the process comprising:
    placing a non-powdered metallic iron in a solution for producing the ferrous picrate.

2. The process according to claim 1, wherein the non-powdered metallic iron is wire or steel wool.

3. The process according to claim 1, wherein the placing the non-powdered metallic iron in the solution is done such that the non-powdered metallic iron is on a bottom of a container holding the solution.

4. The process according to claim 1, wherein the placing the non-powdered metallic iron in the solution is done such that the non-powdered metallic iron is suspended in the solution.

5. The process according to claim 1, the process further comprising:
    agitating the solution containing the non-powdered metallic iron.

6. The process according to claim 1, wherein the solution comprises picric acid.

7. The process according to claim 1, wherein:
    the solution for producing the ferrous picrate is produced by a process comprising:
    dissolving picric acid in a solvent selected from the group consisting of aromatic solvents, high aromatic petroleum fractions, and combinations thereof;
    agitating the solvent including the dissolved picric acid;
    removing water from the solvent including the dissolved picric acid;
    adding an aliphatic alcohol to the solvent including the dissolved picric acid;
    agitating the solvent including the dissolved picric acid and the aliphatic alcohol;
    adding 0.1 to 0.5 percent water to the solvent including the dissolved picric acid and the aliphatic alcohol; and
    agitating the solvent including the dissolved picric acid, the aliphatic alcohol and the 0.1 to 0.5 percent water to produce the solution for producing the ferrous picrate.

8. The process according to claim 1, the process further comprising:
    adding a pre-mix solution to the solvent including the dissolved picric acid, the aliphatic alcohol, and the 0.1 to 0.5 percent water, wherein the pre-mix solution is produced by the process comprising:
    dissolving picric acid in another fraction of solvent selected from the group consisting of aromatic solvents, high aromatic petroleum fractions, and combinations thereof;
    removing water from the another fraction of the solvent having the dissolved picric acid; and
    adding an aliphatic alcohol to the another fraction of the solvent having the dissolved picric acid, such that a resulting solution comprises about 1.9 percent free picric acid and about 15 to 16 percent of the aliphatic alcohol.

* * * * *